(12) United States Patent
Wu et al.

(10) Patent No.: US 8,980,624 B2
(45) Date of Patent: Mar. 17, 2015

(54) APPARATUS FOR HIGH-THROUGHPUT CELL CULTURE WITH MECHANICAL COMPRESSION STIMULATION

(75) Inventors: Min-Hsien Wu, Kaohsiung (TW); Chun-Li Lin, Tao-Yuan (TW); Shiao-Wen Tsai, Tao-Yuan (TW); Heng-Liang Liu, Tao-Yuan (TW); Yen-Ting Liu, Tao-Yuan (TW)

(73) Assignee: Chang Gung University, Tao-Yuan (TW)

( * ) Notice: Subject to any disclaimer, the term of this patent is extended or adjusted under 35 U.S.C. 154(b) by 965 days.

(21) Appl. No.: 12/651,905

(22) Filed: Jan. 4, 2010

(65) Prior Publication Data

US 2011/0076758 A1   Mar. 31, 2011

(30) Foreign Application Priority Data

Sep. 29, 2009  (TW) .............................. 98132918 A

(51) Int. Cl.
| | | |
|---|---|---|
| *C12M 1/00* | (2006.01) | |
| *C12M 3/00* | (2006.01) | |
| *C12M 3/06* | (2006.01) | |
| *C12M 1/12* | (2006.01) | |
| *C12M 1/42* | (2006.01) | |

(52) U.S. Cl.
CPC ............... *C12M 23/44* (2013.01); *C12M 29/10* (2013.01); *C12M 29/14* (2013.01); *C12M 35/04* (2013.01)

USPC .................. 435/297.1; 435/283.1; 435/289.1; 435/295.3

(58) Field of Classification Search
USPC .............................................. 435/283.1–309.4
See application file for complete search history.

(56) References Cited

U.S. PATENT DOCUMENTS

| | | | | |
|---|---|---|---|---|
| 5,153,136 A | * | 10/1992 | Vandenburgh | 435/286.1 |
| 6,048,723 A | * | 4/2000 | Banes | 435/305.1 |
| 6,576,458 B1 | * | 6/2003 | Sarem et al. | 435/286.5 |
| 6,653,124 B1 | * | 11/2003 | Freeman | 435/297.1 |
| 2006/0270023 A1 | * | 11/2006 | LeDuc et al. | 435/289.1 |
| 2009/0088342 A1 | * | 4/2009 | Moraes et al. | 506/12 |

* cited by examiner

*Primary Examiner* — Nathan Bowers
*Assistant Examiner* — Lydia Edwards
(74) *Attorney, Agent, or Firm* — Foley & Lardner LLP; Andrew S. Baluch

(57) ABSTRACT

An apparatus for high-throughput cell culture with mechanical compression stimulation includes a cell culture vessel and a fluid pressure supply unit. The cell culture vessel includes at least one culture chamber, at least one pressure chamber disposed above the culture chamber, a membrane disposed between the culture chamber and the pressure chamber, and at least one pressurizing member that projects downwardly from the membrane into the culture chamber. The fluid pressure supply unit is connected fluidly to the pressure chamber, and has a fluid pressure supply device to supply a pressurized fluid to the pressure chamber so as to deform the membrane and move the pressurizing member, and a control device that is adapted to vary a pressure of the pressurized fluid in the pressure chamber.

11 Claims, 4 Drawing Sheets

US 8,980,624 B2

APPARATUS FOR HIGH-THROUGHPUT CELL CULTURE WITH MECHANICAL COMPRESSION STIMULATION

CROSS-REFERENCE TO RELATED APPLICATION

This application claims priority of Taiwanese application no. 098132918, filed on Sep. 29, 2009.

BACKGROUND OF THE INVENTION

1. Field of the Invention

This invention relates to an apparatus for cell culture, more particularly to an apparatus for high-throughput cell culture with mechanical compression stimulation.

2. Description of the Related Art

Examples of conventional bioreactors used for tissue engineering are spinner flask bioreactors, rotating-wall vessels, hollow-fiber bioreactors, perfusion bioreactors, and so forth. Continuously, simultaneously, and equivalently importing a fresh culture medium into a culture vessel and exporting a waste culture medium out of the culture vessel can be regarded as perfusion culture. Consequently, a volume of a culture medium in the aforementioned culture vessel can be maintained constant. Accordingly, a conventional perfusion cell culture system is able to provide a steady and quantifiable culture condition that is favorable for establishing a quantitative link between an extracellular stimulus and a cellular response.

However, the conventional perfusion cell culture system has a large size and a high production cost, is not configured to be easily operated, and is not appropriate for high throughput applications. The disadvantages of the conventional perfusion cell culture system may limit a range of applications of the same.

Furthermore, in order to investigate a relationship between mechanical compression stimulation and cell physiology, a new miniature device that is suitable for perfusion cell culture, that can overcome the aforementioned disadvantages of the conventional perfusion cell culture system, and that is capable of providing mechanical compression stimulation, is required. For example, the new miniature device can be operated to examine how mechanical compression stimulation may influence differentiation of stem cells or tissue growth regarding tissue engineering.

SUMMARY OF THE INVENTION

Therefore, the object of the present invention is to provide an apparatus for high-throughput cell culture with mechanical compression stimulation in order to overcome the aforesaid drawbacks of the prior art.

According to this invention, an apparatus for high-throughput cell culture with mechanical compression stimulation includes a cell culture vessel and a fluid pressure supply unit. The cell culture vessel includes at least one culture chamber, at least one pressure chamber disposed above the culture chamber, a membrane that is disposed between the culture chamber and the pressure chamber, and at least one pressurizing member that projects downwardly from the membrane into the culture chamber. The fluid pressure supply unit is connected fluidly to the pressure chamber, and has a fluid pressure supply device to supply a pressurized fluid to the pressure chamber so as to deform the membrane and move the pressurizing member, and a control device that is adapted to vary a pressure of the pressurized fluid in the pressure chamber.

BRIEF DESCRIPTION OF THE DRAWINGS

Other features and advantages of the present invention will become apparent in the following detailed description of the preferred embodiment of this invention, with reference to the accompanying drawings, in which.

DETAILED DESCRIPTION OF THE PREFERRED EMBODIMENT

Figure 1:
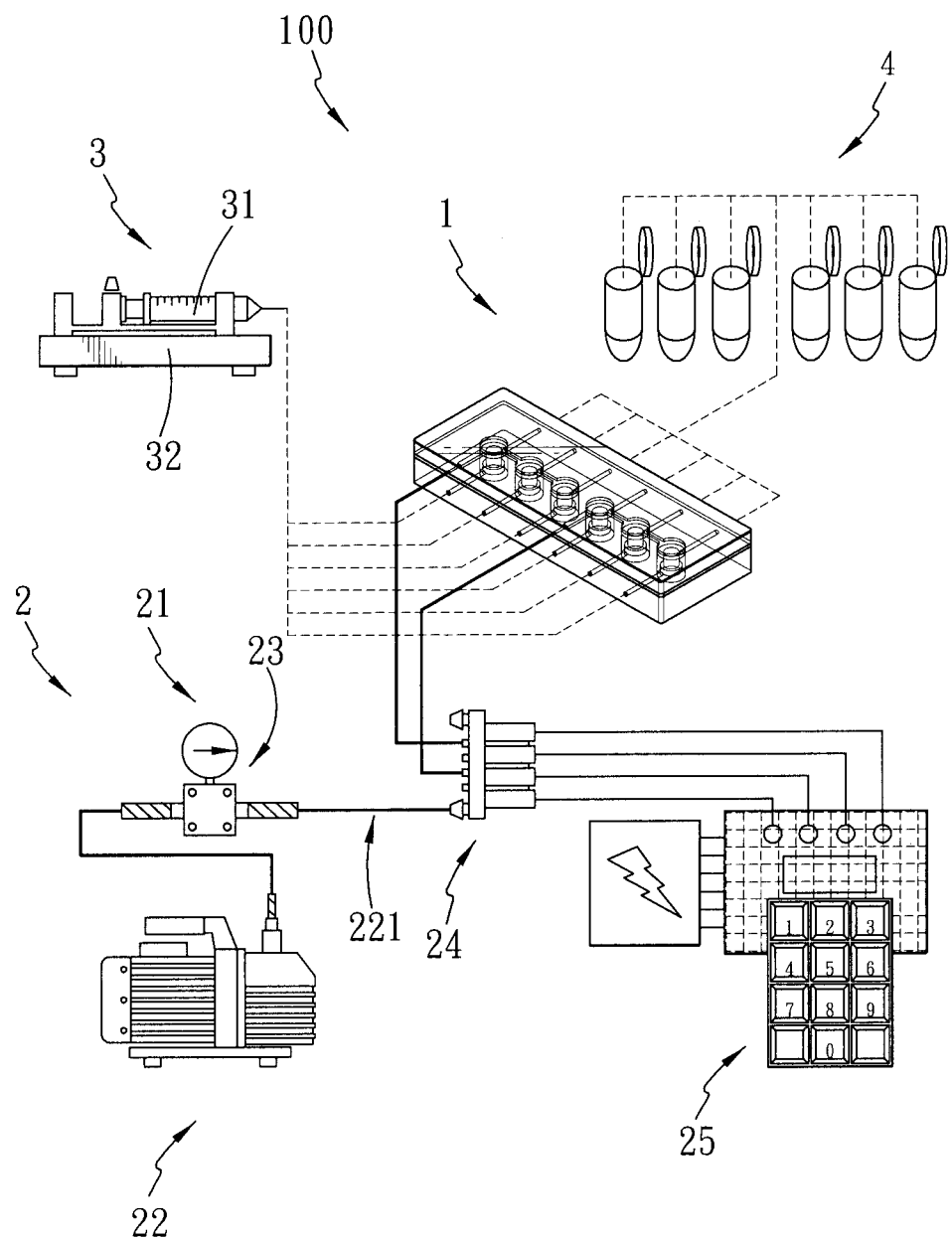
FIG. 1 is a schematic diagram of the preferred embodiment of an apparatus for high-throughput cell culture with mechanical compression stimulation according to this invention.
Figure 2:
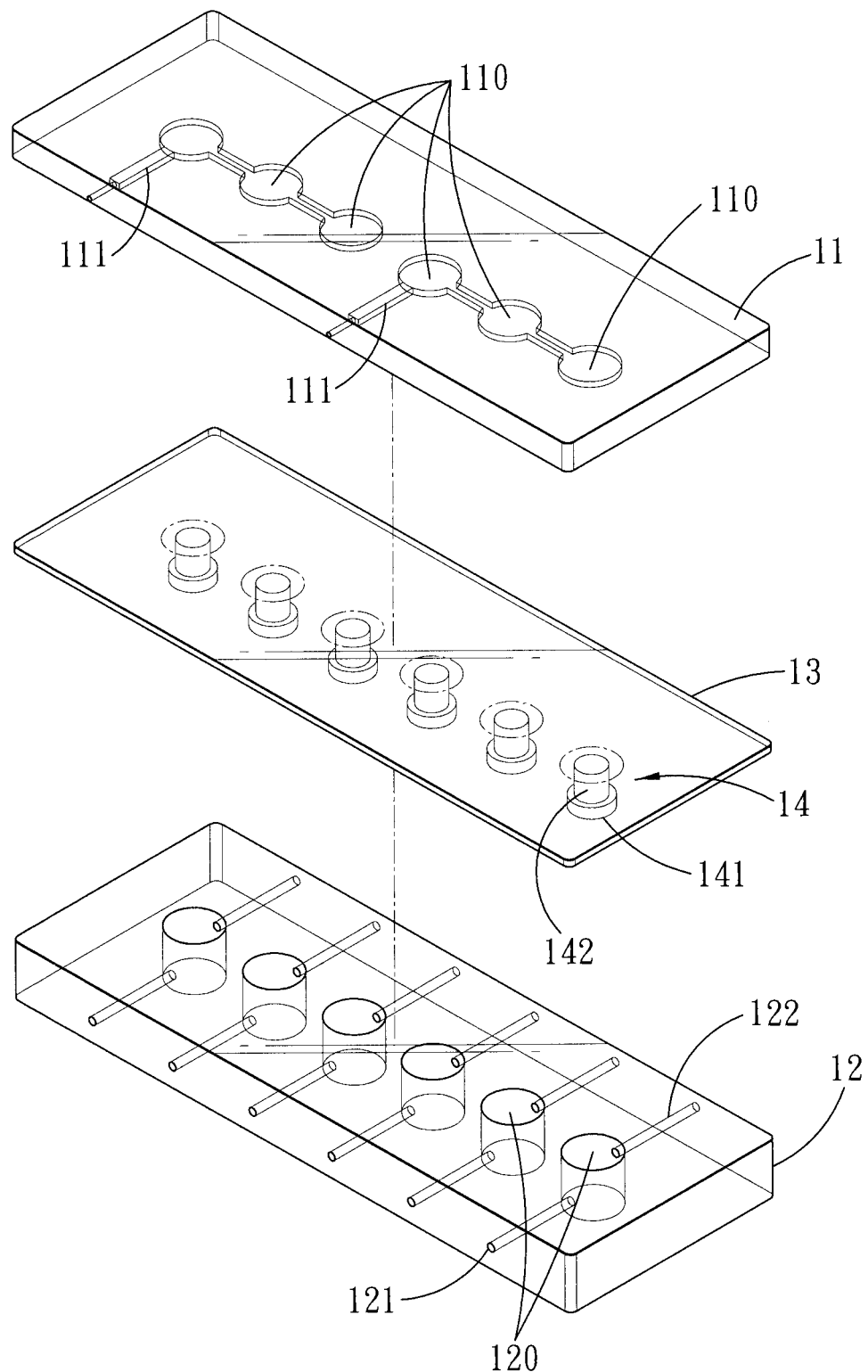
FIG. 2 is an exploded perspective view to illustrate a cell culture vessel of the apparatus according to the preferred embodiment.
Figure 3:
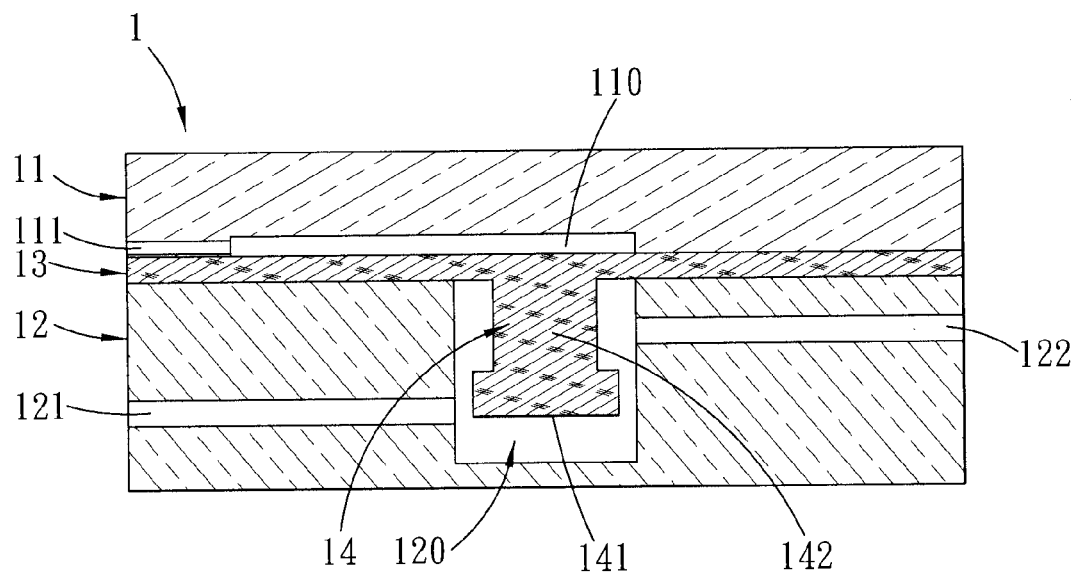
FIG. 3 is a sectional view to illustrate the cell culture vessel of the apparatus according to the preferred embodiment.

Referring to FIGS. 1, 2, and 3, according to the present invention, the preferred embodiment of an apparatus 100 for high-throughput cell culture with mechanical compression stimulation is a perfusion cell culture apparatus, and includes a cell culture vessel 1 and a fluid pressure supply unit 2.

Preferably, the cell culture vessel 1 is a multi-layered structure including a top layer 11 which has six pressure chambers 110, a base layer 12 which has six culture chambers 120 that are adapted to contain cells and a culture medium, and a middle layer which is a membrane 13 and which is disposed between the top layer 11 and the base layer 12. The pressure chambers 110 are disposed respectively above the culture chambers 120. The membrane 13 is disposed between the culture chambers 120 and the pressure chambers 110. The three consecutive pressure chambers 110 on the right are in spatial communication with each other, and the other three consecutive pressure chambers 110 on the left are in spatial communication with each other. Six pressurizing members 14 are connected to the membrane 13, are formed as one piece with the middle layer, and project downwardly from the membrane 13 into the culture chambers 120, respectively.

Preferably, each of the pressurizing members 14 has a pillar portion 142 that projects downwardly from the membrane 13 into a respective one of the culture chambers 120. In this embodiment, a bottom part of each of the pressurizing members 14 is an enlarged disc portion 141 that is formed at a bottom end of the pillar portion 142. A bottom face of the enlarged disc portion 141 is adapted to exert a uniform mechanical compression force on the cells.

The top layer 11, the base layer 12, the membrane 13, and the pressurizing members 14 are all made from an elastomer (such as polydimethylsiloxane), and are formed by casting or other fabrication techniques. In the case of casting, desired molds are first produced. Afterward, a molding composition containing the elastomer is cast in the molds to form the top and base layers 11, 12 and the middle layer, which are then assembled together by adhesive bonding to form a unitary body. A surface treatment (e.g., plasma oxidation) is conducted to improve the adhesive bonding.

The fluid pressure supply unit 2 is connected fluidly to the pressure chambers 110, and has a fluid pressure supply device 22 to supply a pressurized fluid (not shown) to the pressure chambers 110 through a piping unit 221 for moving the membrane 13 and the pressurizing members 14, and a control device 21 that is adapted to vary a pressure of the pressurized fluid. In this embodiment, the fluid pressure supply device 22 is a pneumatic device that supplies a pressurized gas. It should be noted that the fluid pressure supply device 22 could be a hydraulic device that supplies a pressurized liquid in other embodiments.

The control device 21 of the fluid pressure supply unit 2 includes a flow regulator 23 connected to the piping unit 221 so as to regulate the flow of the pressurized fluid in the piping unit 221, and a set of electro-magnetic valves 24 connected to the piping unit 221 to control the pressurized fluid so that the pressurized fluid enters intermittently into the pressure chambers 110. The control device 21 further includes a control module 25 to control alternate opening and closing of the electro-magnetic valves 24, and to control the flow regulator 23, thereby varying the fluid pressure in the pressure chambers 110. The frequency and magnitude of mechanical compression stimulation for cells can therefore be controlled.

The apparatus 100 further includes a culture medium supply device 3 that is connected fluidly to the culture chambers 120 of the base layer 12 and that is adapted to supply a culture medium (not shown) to the culture chambers 120, and a culture medium collecting device 4 that is connected fluidly to the culture chambers 120 and that is adapted to collect the culture medium from the culture chambers 120. In this embodiment, the culture medium supply device 3 includes a syringe 31 adapted to contain the culture medium, and a syringe pump 32 to actuate a plunger of the syringe 31 for expelling the culture medium out of the syringe 31. By means of the culture medium supply device 3, a predetermined amount of the culture medium can be supplied to the cells in the culture chambers 120 at predetermined intervals. It is noted that the culture medium supply device 3 can be a multi-syringe infusion pump or a peristaltic pump in other preferred embodiments.

The base layer 12 further has an inflow channel unit that has six inflow channels 121 in fluid communication with the culture chambers 120 and the culture medium supply device 3, and an outflow channel unit that has six outflow channels 122 in fluid communication with the culture chambers 120 and the culture medium collecting device 4. The outflow channels 122 are higher than the inflow channels 121. Six inflow metal tubes (not shown) are respectively inserted into the six inflow channels 121 and are respectively connected to six inflow silica gel tubes (not shown) that are connected to the culture medium supply device 3. Similarly, six outflow metal tubes (not shown) are respectively inserted into the six outflow channels 122 and are respectively connected to six outflow silica gel tubes (not shown) that are connected to the culture medium collecting device 4.

Figure 4:
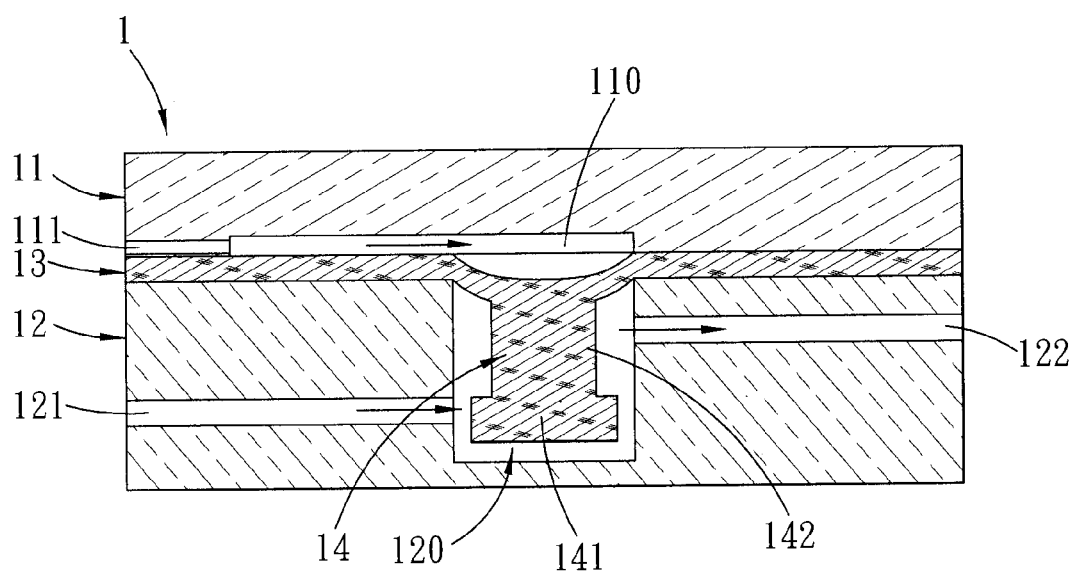
FIG. 4 is the same view as FIG. 3 but illustrating that a membrane of the cell culture vessel is elastically deformed by a fluid pressure so as to move a pressurizing member of the cell culture vessel.
Figure 5:
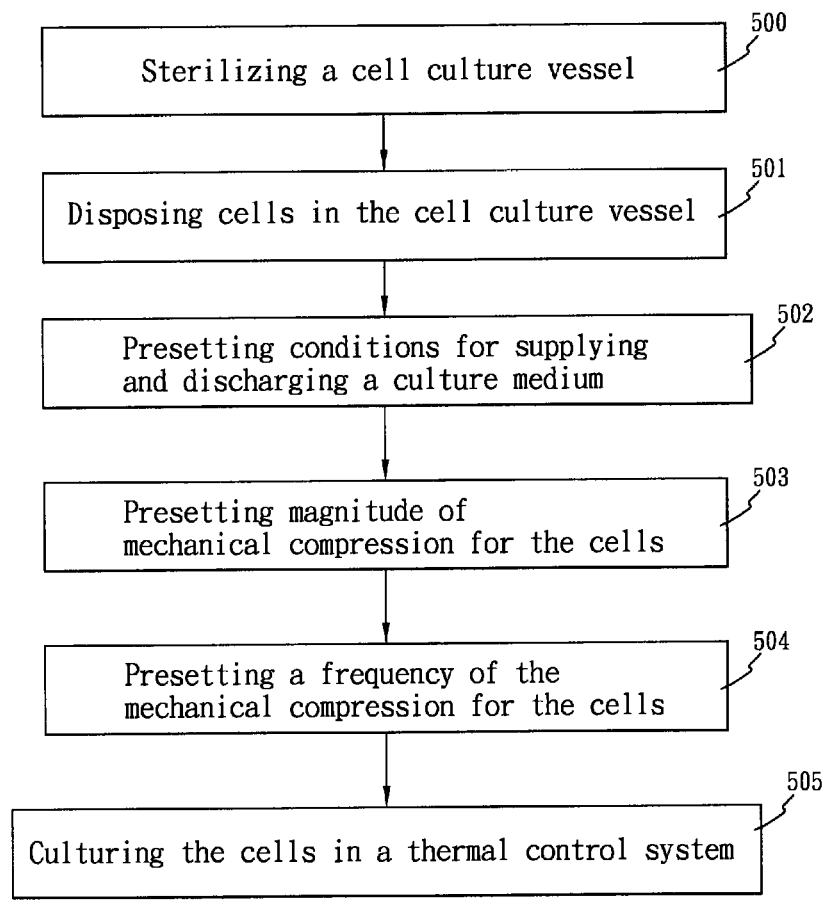
FIG. 5 is a flow chart to illustrate a method of operating the apparatus according to the preferred embodiment.

Referring to FIGS. 1, 2, and 4, the fresh culture medium flows into the culture chambers 120 from the culture medium supply device 3 through the inflow channels 121 at a lower position. The waste culture medium flows to the culture medium collecting device 4 from the culture chambers 120 via the outflow channels 122 when the level of the culture medium rises to a higher level. Therefore, a constant environment is established for growth of the cells due to continuous supply of the fresh culture medium and continuous removal of the waste culture medium. A steady and quantifiable culture condition is achieved as well.

The top layer 11 further has a flow channel unit that has two flow channels 111, each of which is in fluid communication with three of the pressure chambers 110 and the fluid pressure supply unit 2. Two metal tubes (not shown) are respectively inserted into the flow channels 111, and are respectively connected to two silica gel tubes (not shown) that are connected to the fluid pressure supply unit 2. The pressurized fluid is introduced into the pressure chambers 110 by virtue of the flow channels 111 such that the membrane 13 is pushed intermittently. When the membrane 13 is pushed and deformed downwardly (see FIG. 4), the pressurizing members 14 are moved downwardly in the respective culture chambers 120, thereby exerting a mechanical compression force on the cells.

Two-dimensional (2-D) and three-dimensional (3-D) cell culture can be conducted by virtue of the apparatus 100. The cells can be attached to bottom surfaces of the culture chambers 120 so as to perform 2-D cell culture. Alternatively, the cells can be encapsulated in a 3-D material (e.g., hydrogel) and disposed in the culture chambers 120 to perform 3-D cell culture. Mechanical compression stimulation can be hence applied to both 2-D and 3-D cell culture.

Referring to FIGS. 1 to 5, a method of operating the apparatus 100 is described as follows. In step 500, the cell culture vessel 1 is sterilized before disposing the cells in the culture chambers 120. Alcohol, a retort (such as an autoclave), UV light, a suitable gas, or other sterilization means can be utilized to sterilize the cell culture vessel 1. In step 501, the cells are disposed in the cell culture vessel 1 by attaching the same to the bottom surfaces of the culture chambers 120 for 2-D cell culture. Examples of the cells are articular chondrocytes or other cells appropriate for mechanical compression stimulation. In step 502, conditions (e.g., flow rates) for supplying and discharging the culture medium are preset. In step 503, magnitude of mechanical compression for the cells is preset by controlling the flow regulator 23. In step 504, a frequency of the mechanical compression for the cells is preset by controlling the electro-magnetic valves 24 and the control module 25.

In step 505, the cell culture vessel 1 is disposed in a thermal control system such as an incubator so as to culture the cells while the mechanical compression forces are applied to the cells for stimulation. Specifically, the membrane 13 is pushed and deformed intermittently by the pressurized fluid, thereby moving the pressurizing members 14 downwardly and intermittently and producing downward compression forces to stimulate the cells. By alternately increasing and decreasing the fluid pressure through the control of the electro-magnetic valves 24 and the flow regulator 23, the pressurizing members 14 can produce compression forces with varying frequency and strength.

The cell culture vessel 1 is able to be miniaturized, is suitable for high throughput applications, can be easily operated with the fluid pressure supply unit 2 to provide mechanical compression stimulation, and has a low production cost. Consequently, the cell culture vessel 1 is suitable to be further developed into a disposable cell culture device.

By controlling the membrane 13 through the fluid pressure device 22 and the control device 21, the strength and frequency of the mechanical compression forces for stimulation of the cells can be varied and adjusted.

While the present invention has been described in connection with what are considered the most practical and preferred embodiments, it is understood that this invention is not limited to the disclosed embodiments but is intended to cover various arrangements included within the spirit and scope of the broadest interpretation and equivalent arrangements.

What is claimed is:

1. An apparatus for high-throughput cell culture with mechanical compression stimulation, comprising:
  a cell culture vessel including at least one culture chamber adapted to culture at least one cell, at least one pressure chamber disposed above said culture chamber, a membrane disposed between said at least one culture chamber and said at least one pressure chamber, and at least one pressurizing member that has a pillar portion projecting downwardly from said membrane into said at least one culture chamber; and
  a fluid pressure supply unit connected fluidly to said at least one pressure chamber and having a fluid pressure supply device to supply a pressurized fluid to said at least one pressure chamber to deform said membrane and move said at least one pressurizing member, and
  a control device to vary a pressure of the pressurized fluid in said at least one pressure chamber; and
  an outflow channel that is in fluid communication with said at least one culture chamber, and an inflow channel that is in fluid communication with said at least one culture chamber, said inflow channel being disposed at a position that is higher than a bottom surface of said at least one culture chamber and that is lower than said outflow channel,
  wherein said pillar portion has a bottom free end for applying a mechanical compression force to said cell, said bottom free end having an enlarged disc portion that has a cross section larger than a cross section of a remaining part of said pillar portion.

2. The apparatus as claimed in claim 1, wherein said cell culture vessel is a multi-layered structure comprising:
  a top layer comprising the at least one pressure chamber,
  a base layer comprising the at least one culture chamber respectively disposed below said at least one pressure chamber, and
  a middle layer forming said membrane,
  wherein the at least one pressurizing member comprises a plurality of pressurizing members being formed as one piece with said middle layer and protruding into said at least one culture chamber, respectively.

3. The apparatus as claimed in claim 1, wherein said control device of said fluid pressure supply unit includes:
  a flow regulator to regulate flow of the pressurized fluid;
  an electro-magnetic valve for controlling the pressurized fluid so that the pressurized fluid enters intermittently into said at least one pressure chamber; and
  a control module for controlling alternate opening and closing of said electro-magnetic valve to vary frequency of fluid pressure input in said at least one pressure chamber.

4. The apparatus as claimed in claim 2, wherein said top layer further comprises a flow channel unit that is in fluid communication with said at least one pressure chamber and said fluid pressure supply unit.

5. The apparatus as claimed in claim 2, further comprising:
  a culture medium supply device connected fluidly to said at least one culture chamber of said base layer and adapted to supply a culture medium to said at least one culture chamber, and
  a culture medium collecting device connected fluidly to said at least one culture chamber and adapted to collect the culture medium from said at least one culture chamber.

6. The apparatus as claimed in claim 5, wherein:
  said base layer comprises the inflow channel and the outflow channel,
  the inflow channel is in fluid communication with said culture medium supply device, and
  the outflow channel is in fluid communication with said culture medium collecting device.

7. The apparatus as claimed in claim 1, wherein said fluid pressure supply device is a pneumatic device.

8. The apparatus as claimed in claim 1, wherein said fluid pressure supply device is a hydraulic device.

9. The apparatus as claimed in claim 2, wherein said middle layer of said cell culture vessel is made from an elastomer.

10. The apparatus as claimed in claim 1, further comprising:
  an outflow channel and an inflow channel, wherein the outflow channel is in fluid communication with said at least one culture chamber at a position higher than a bottom surface of said at least one culture chamber, said bottom end of said pillar portion extending toward said bottom surface to a level proximate to said position of said inflow channel.

11. An apparatus for high-throughput cell culture with mechanical compression stimulation, comprising:
  a cell culture vessel including at least one culture chamber adapted to culture cells, at least one pressure chamber disposed above said at least one culture chamber, a membrane disposed between said at least one culture chamber and said at least one pressure chamber, and at least one pressurizing member that has a pillar portion projecting downwardly from said membrane into said at least one culture chamber, and an enlarged disc portion formed at a bottom end of said pillar portion and having a cross section that is larger than that of said pillar portion, said enlarged disc portion further having a bottom compression surface facing a bottom surface of said at least one culture chamber;
  a fluid pressure supply unit connected fluidly to said at least one pressure chamber and having a fluid pressure supply device to supply a pressurized fluid to said at least one pressure chamber so as to deform said membrane and move said at least one pressurizing member, and a control device to vary a pressure of the pressurized fluid in said at least one pressure chamber; and
  an outflow channel and an inflow channel, both of which are in fluid communication with said at least one culture chamber, said inflow channel being disposed at a position higher than said bottom surface of said at least one culture chamber and lower than said outflow channel, wherein:
  said pillar portion is movable upward and downward to move said enlarged disc portion between a highest position and a lowest position,
  said outflow channel is disposed at a level higher than said enlarged disc portion in said highest position, and
  said inflow channel is disposed at a level higher than said bottom compression surface of said enlarged disc portion in said lowest position.

* * * * *